United States Patent
Chiba et al.

(10) Patent No.: US 8,182,745 B2
(45) Date of Patent: May 22, 2012

(54) AUTOMATIC ANALYZER

(75) Inventors: Hideyasu Chiba, Hitachinaka (JP);
Katsuaki Takahashi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 218 days.

(21) Appl. No.: 12/200,443

(22) Filed: Aug. 28, 2008

(65) Prior Publication Data

US 2009/0068063 A1    Mar. 12, 2009

(30) Foreign Application Priority Data

Aug. 29, 2007  (JP) ................. 2007-221989

(51) Int. Cl.
*G01N 21/00* (2006.01)
(52) U.S. Cl. ............... 422/63; 422/64; 422/65; 422/66; 422/67; 210/634; 73/864.01
(58) Field of Classification Search ............ 422/63–67, 422/99–100, 500–502; 210/634; 73/864.1
See application file for complete search history.

(56) References Cited

U.S. PATENT DOCUMENTS

| | | | | |
|---|---|---|---|---|
| 3,748,911 | A | * | 7/1973 | Rousselet et al. .......... 73/864.22 |
| 4,713,218 | A | | 12/1987 | Schwartz |
| 4,751,052 | A | | 6/1988 | Schwartz |
| 4,803,050 | A | | 2/1989 | Mack |
| 5,268,103 | A | * | 12/1993 | Jameson et al. .............. 210/634 |
| 2005/0014274 | A1 | | 1/2005 | Lee et al. |

FOREIGN PATENT DOCUMENTS

JP    10-062431    3/1998

* cited by examiner

*Primary Examiner* — Jyoti Nagpaul
(74) *Attorney, Agent, or Firm* — Mattingly & Malur, P.C.

(57) ABSTRACT

An automatic analyzer having a positioning member connected to a nozzle support jig used to install a rinse nozzle having a suction member. The positioning member is present at a lower position than that of the suction member, has a vertically movable construction, and during a downward movement of the rinse mechanism, is brought close to/inserted into the reaction cuvette earlier than the suction member. Thus, the positioning member adjusts an inserting position of the suction member appropriately if the stopping position of the reaction cuvette deviates.

2 Claims, 8 Drawing Sheets

AUTOMATIC ANALYZER

INCORPORATED BY REFERENCE

The present application claims priority from Japanese application 2007-221989 filed on Aug. 29, 2007, the contents of which are hereby incorporated by reference into this application.

BACKGROUND OF THE INVENTION

1. Field of the Invention

The present invention relates generally to automatic analyzers for analyzing biological samples such as blood and urine, and more particularly, to an automatic analyzer with a rinse mechanism for rinsing a reaction cuvette.

2. Description of the Related Art

Automatic analyzers that conduct qualitative and/or quantitative analyses on a biological sample such as blood or urine cause the sample and a reagent to react in a reaction cuvette and analyze the constituents of the sample that are to be measured. After one measuring operation, the reaction cuvette formed of a material such as a plastic or glass is generally rinsed for reuse. The reaction cuvette, after being moved to a required rinsing position, is usually rinsed by suctioning the reaction liquid (the liquid left as a waste liquid after the measurement) with a nozzle, then repeating injection and suction of water, rinse water, or the like a required number of times, and finally suctioning the rinse water. In order to prevent the rinse water from remaining in the reaction cuvette after the rinsing thereof, a suction member formed to extend along the inner wall of the reaction cuvette is installed at the tip of a rinsing nozzle. JP-A-10-062431 describes a technique for forming a suction member to minimize the amount of rinse water left unsuctioned.

SUMMARY OF THE INVENTION

As described in JP-A-10-062431, the clearance between the rinse nozzle tip and the inner wall of the reaction cuvette is commonly made as small as possible for a minimum amount of rinse water left unsuctioned. Meanwhile, the positioning accuracy of the reaction cuvette in the rinsing position is required to be higher as the clearance is reduced. Automatic analyzers are required to be miniaturized, to be enhanced in throughput and in operating speed, and to employ a more compact reaction cuvette for the use of samples and reagents in microquantities. These requirements are placed under the relationship of trade-offs with respect to the improvement of reaction cuvette stopping position accuracy, and merely reducing the clearance increases a chance of nozzle tip trouble due to a collision with the reaction cuvette.

An object of the present invention is to provide a highly reliable automatic analyzer comprising a rinse mechanism adapted such that a suction member is reliably inserted into a reaction cuvette without deterioration of rinse liquid suction performance, without dimensional increases of the reaction cuvette or of the apparatus, and without being affected by stopping position accuracy of the reaction cuvette.

In order to achieve the above object, the present invention has the following configuration:

An automatic analyzer comprises a reaction cuvette for mixing a sample and a reagent, a reaction disk for setting up the reaction cuvette thereon and transferring the reaction cuvette to a rinsing position, a rinse nozzle that suctions rinse water in the reaction cuvette, a suction member connected to the rinse nozzle, and a shifter for moving the rinse nozzle; wherein the analyzer is further provided with a controller which, in accordance with the position of a positioning guide provided on the reaction cuvette, controls the shifter such that the rinse nozzle is inserted into the cuvette.

A more specific example is shown below. In an automatic analyzer comprising at least a reaction cuvette for mixing a sample and a reagent; a reaction disk for setting up the reaction cuvette thereon and transferring the cuvette to a rinsing position; and a rinse mechanism comprising a rinse nozzle that suctions and discharges rinse water injected into the reaction cuvette, a suction member connected to a tip of the rinse nozzle, a nozzle support jig for supporting the rinse nozzle, a vertically moving arm fastened to the nozzle support jig, a shifter including a feed screw to move the arm vertically, and a motor, the nozzle support jig for installing the rinse liquid suction nozzle to which the suction member is connected includes a positioning member, which is present at a position lower than that of the suction member, constructed to be vertically movable, tapered at its tip, brought close to/inserted into an adjacent reaction cuvette earlier than the suction member during a downward movement of the rinse mechanism, and adapted to adjust an inserting position of the suction member to a correct position if the stopping position of the reaction cuvette deviates. Additionally, in order to achieve the above object, in the above automatic analyzer according to the present invention, the reaction cuvette includes a convex (or concave) positioning guide pin (or tapered hole), whereas the positioning member has a concave (or convex) tapered hole (or guide pin); wherein the positioning member is present at a position lower than that of the suction member, constructed to be vertically movable, and adapted to adjust an inserting position of the suction member to a correct position if, during a downward movement of the rinse mechanism, the convex (or concave) section of the reaction cuvette and the concave (or convex) section of the positioning member are brought close to/inserted into each other earlier than the suction member is inserted into the reaction cuvette and thus the stopping position of the reaction cuvette deviates.

According to the present invention, a highly reliable automatic analyzer can be provided that allows a rinse water suction member to be reliably inserted into a reaction cuvette during rinsing thereof and adjusts an inserting position of the suction member to a correct position even if the stopping position of the reaction cuvette deviates.

DESCRIPTION OF THE PREFERRED EMBODIMENTS

The object of providing a highly reliable automatic analyzer that comprises a rinse mechanism adapted so that a suction member is reliably inserted into a reaction cuvette without deterioration of rinse liquid suction performance and without dimensional increases of the reaction cuvette or of the apparatus was realized by adding a positioning member to the nozzle support jig of the rinse mechanism.

First Embodiment

Figure 1:
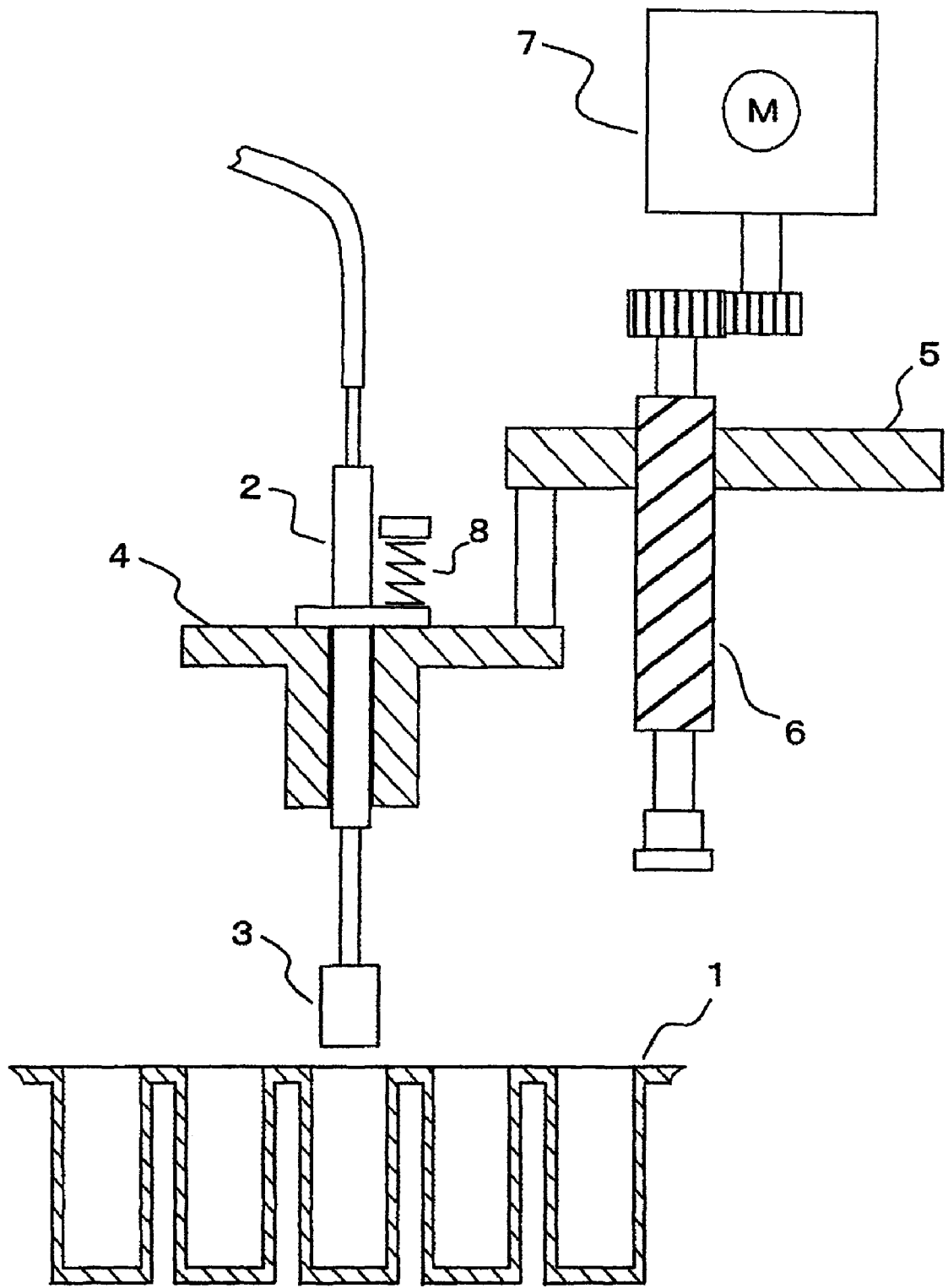
FIG. 1 is a diagram showing a state in which rinse water is not suctioned in a rinse mechanism based on a conventional technique.
Figure 2:
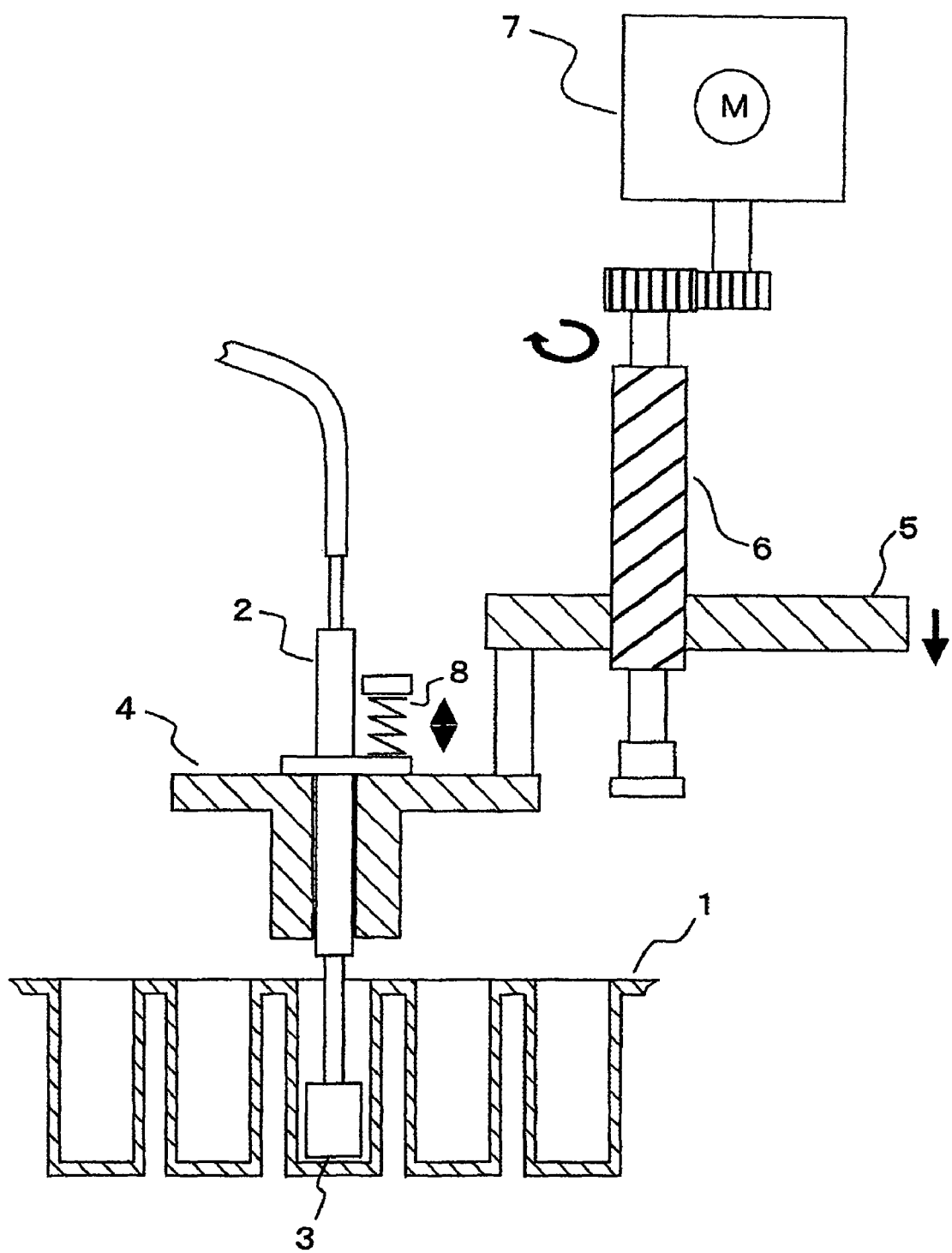
FIG. 2 is a diagram showing a state in which rinse water is suctioned in the rinse mechanism of FIG. 1.

FIGS. 1 and 2 are schematic block diagrams of a conventional rinse mechanism.

Figure 3:
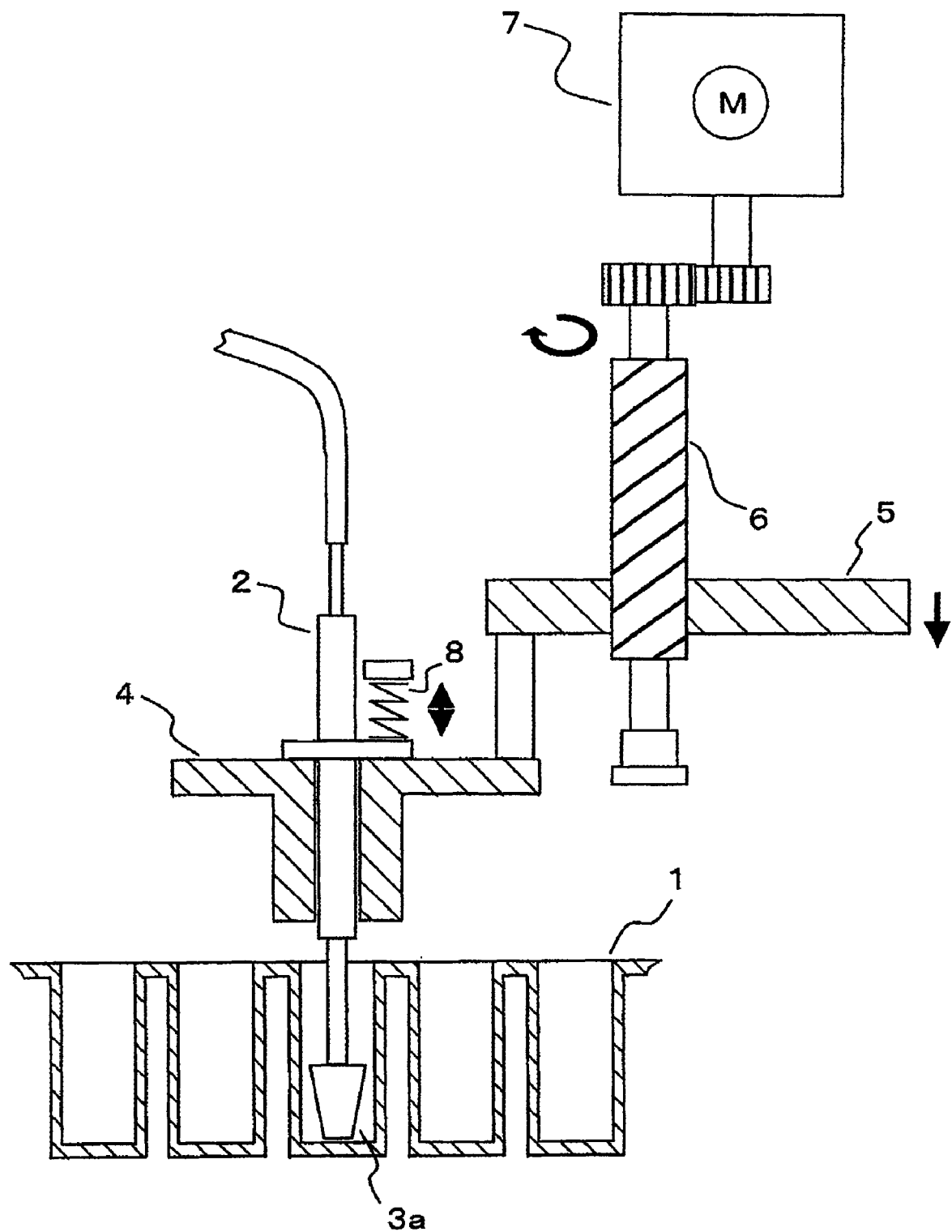
FIG. 3 is a diagram showing a state in which rinse water is suctioned in the rinse mechanism of FIG. 1 that includes a suction member tapered at its tip.
Figure 4:
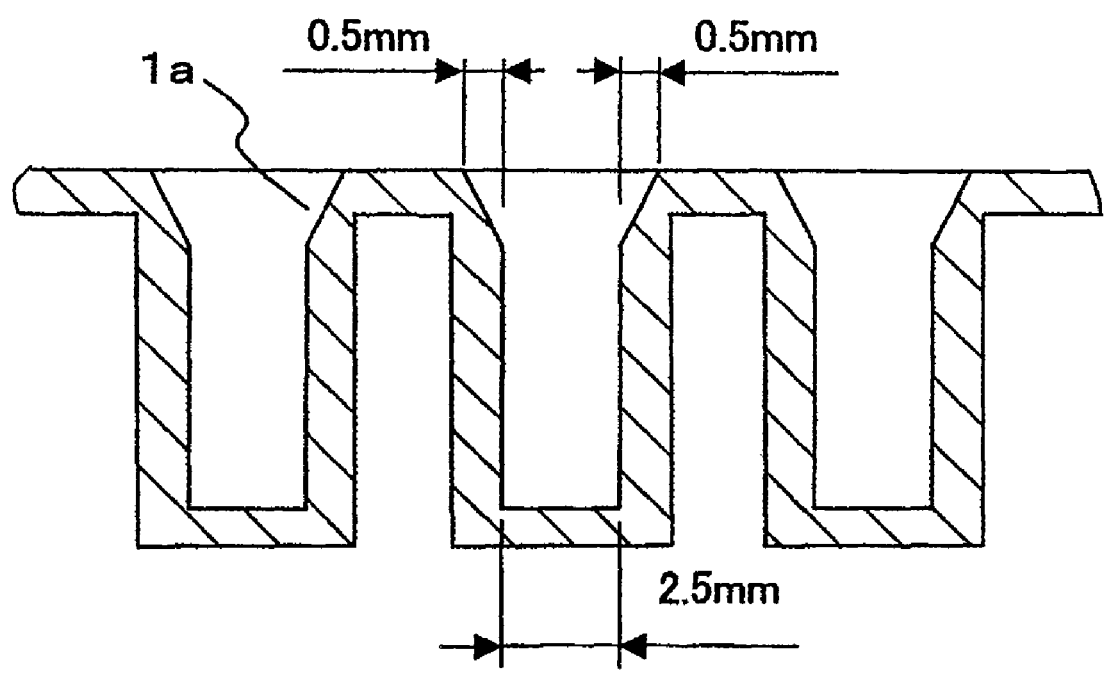
FIG. 4 is a diagram of a tapered entrance of a reaction cuvette.

Referring to FIG. 1, a reaction cuvette 1 is installed on a reaction disk. The rinse mechanism includes elements such as a rinse nozzle 2, a suction member 3 connected to a tip of the rinse nozzle 2, a nozzle support jig 4 for supporting the rinse nozzle 2, an arm 5 fastened to the nozzle support jig 4, a feed screw 6 and motor 7 for moving the arm 5 vertically, and a cushioning spring 8 for the rinse nozzle 2. FIG. 1 shows the state of the rinse mechanism and reaction cuvette existing when rinse water is not suctioned. FIG. 2 shows the state of the rinse mechanism and reaction cuvette existing when rinse water is suctioned. In FIG. 2, downward movement of the arm 5 via the motor 7 and the feed screw 6 also moves downward the nozzle support jig 4 fastened to the arm 5. Thus, the rinse nozzle 2 and suction member 3 connected to the nozzle support jig 4 are also moved downward and inserted into the reaction cuvette 1 that has been moved to a required rinsing position to suction/discharge the rinse water present in the reaction cuvette 1. A clearance between the suction member 3 and an inner wall of the reaction cuvette 1 is very small, so if a stopping position of the reaction cuvette 1 deviates for reasons such as integrated dimensional errors of constituent parts, contact of the suction member 3 with the entrance of the reaction cuvette 1 is likely, which causes an alarm indicating an insertion failure and results in an operational stoppage of the automatic analyzer. To avoid contact between the suction member 3 and the reaction cuvette 1, an inserting position of the suction member 3 can be adjusted conceivably by providing the tip of the suction member with a taper 3a as shown in FIG. 3 or by providing the entrance of the reaction cuvette 1 with a taper 1a as shown in FIG. 4. If the suction member 3 is provided with the taper 3a as shown in FIG. 3, however, the rinse liquid is liable to remain unsuctioned in the reaction cuvette since the clearance between the tapered section and the inner wall of the reaction cuvette will increase. If the entrance of the reaction cuvette 1 is provided with the taper 1a as shown in FIG. 4, since the distance from the starting position of the taper to the ending position thereof needs to be at least about 0.5 mm, the reaction cuvette will be 2.5 to 3.5 mm wide, which is about 1.4 times as wide as in conventional techniques. This increase in the width of the reaction cuvette will increase the spaces between the reaction cuvette and its adjacent reaction cuvettes, hence necessarily increasing the size of the reaction disk on which to set up the cuvettes, and posing problems associated with miniaturization of both the cuvettes and the apparatus.

Accordingly, the operation of a first embodiment of the present invention for solving the above problems will be described using FIGS. 5, 6, 7, and 8.

Figure 5:
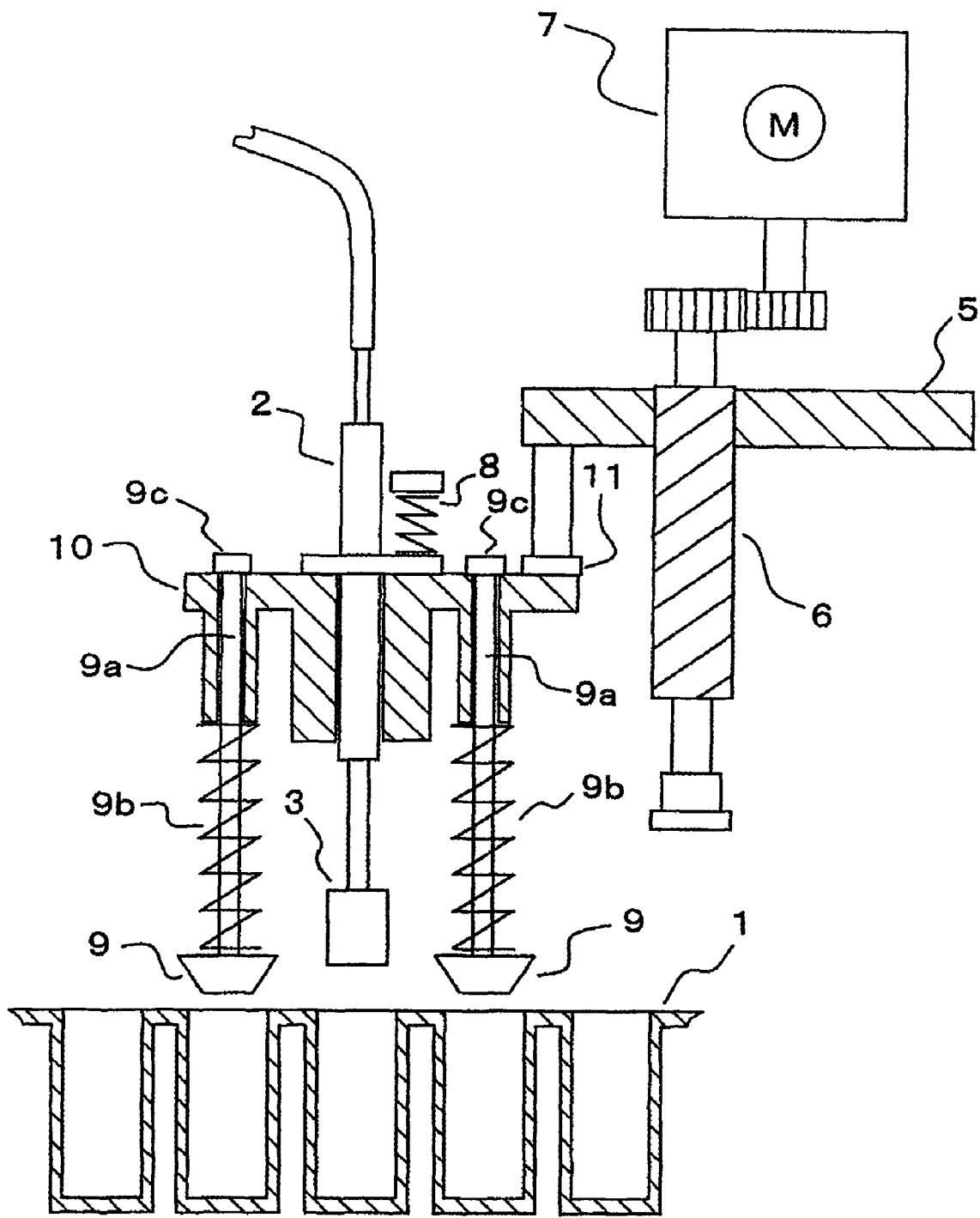
FIG. 5 is a diagram showing a state in which rinse water is not suctioned in a first embodiment of the present invention.
Figure 6:
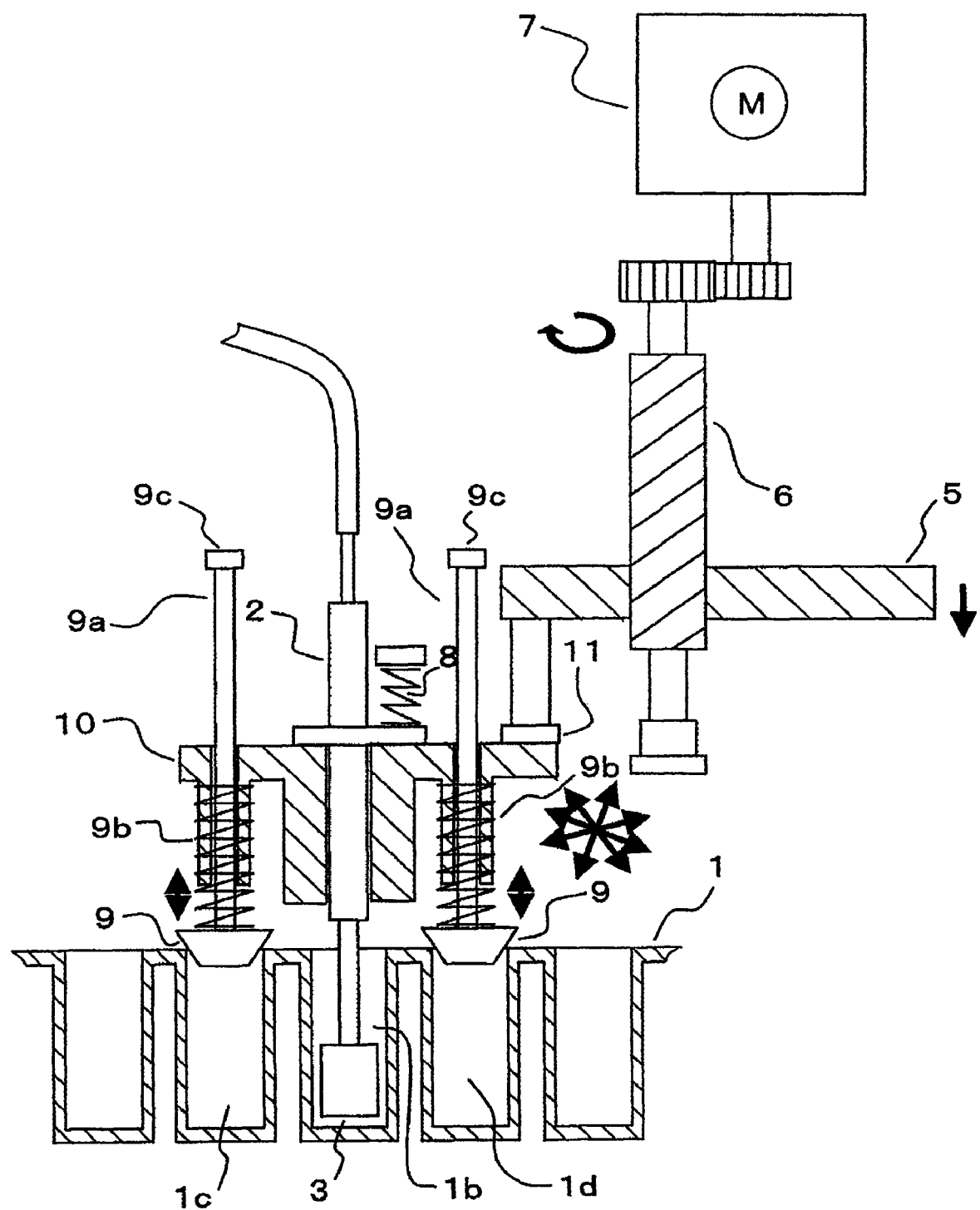
FIG. 6 is a diagram showing a state in which rinse water is suctioned in the first embodiment of the present invention.

Referring to FIG. 5, a positioner includes a positioning member 9, a shaft 9a, a spring 9b, and a retainer 9c, is installed through a nozzle support jig 10, and can be moved vertically. Also, the section at which the nozzle support jig 10 is fastened to an arm 5 has an added movable part 11 so that when a reaction cuvette 1 and the positioning member 9 are guided toward each other, the nozzle support jig 10 can be moved slightly in a horizontal direction. A relationship in position between the positioning member 9 and a suction member 3 is the same as a positional relationship of the reaction cuvette 1 to its adjacent reaction cuvettes. The positioning member 9 when rinse water is not suctioned is positioned to be lower than the suction member 3. FIG. 6 shows a state of the rinse mechanism existing when rinse water is suctioned. In this state, as in the state of FIG. 2, the arm 5, the nozzle support jig 10, a rinse nozzle 2, and the suction member 3 move downward. At this time, although the positioning member 9, the shaft 9a, the spring 9b, and the retainer 9c also descend, since the positioning member 9 is present at a position lower than that of the suction member 3, the positioning member 9 approaches the reaction cuvette 1 earlier. The positioning member 9A descends to a reaction cuvette position 1c or reaction cuvette position 1d adjacent to a reaction cuvette position 1b into which the suction member 3 is inserted. The positioning member 9A has a tapering tip, and a wide clearance is formed between the inner wall of the reaction cuvette 1 and the tip of the positioning member 9. The positioning member 9A is therefore adapted to easily enter the reaction cuvette 1 and adjust an inserting position of the suction member 3 to a correct position. At this time, the movable part 11 assists the nozzle support jig 10 in moving horizontally. Since the suction member 3 and the reaction cuvette 1 are not changed in shape or size, the suction member is thus reliably inserted into the reaction cuvette without deterioration of rinse liquid suction performance and without dimensional increases of the reaction cuvette or of the apparatus. Therefore, high reliability of the automatic analyzer can be achieved.

Figure 7:
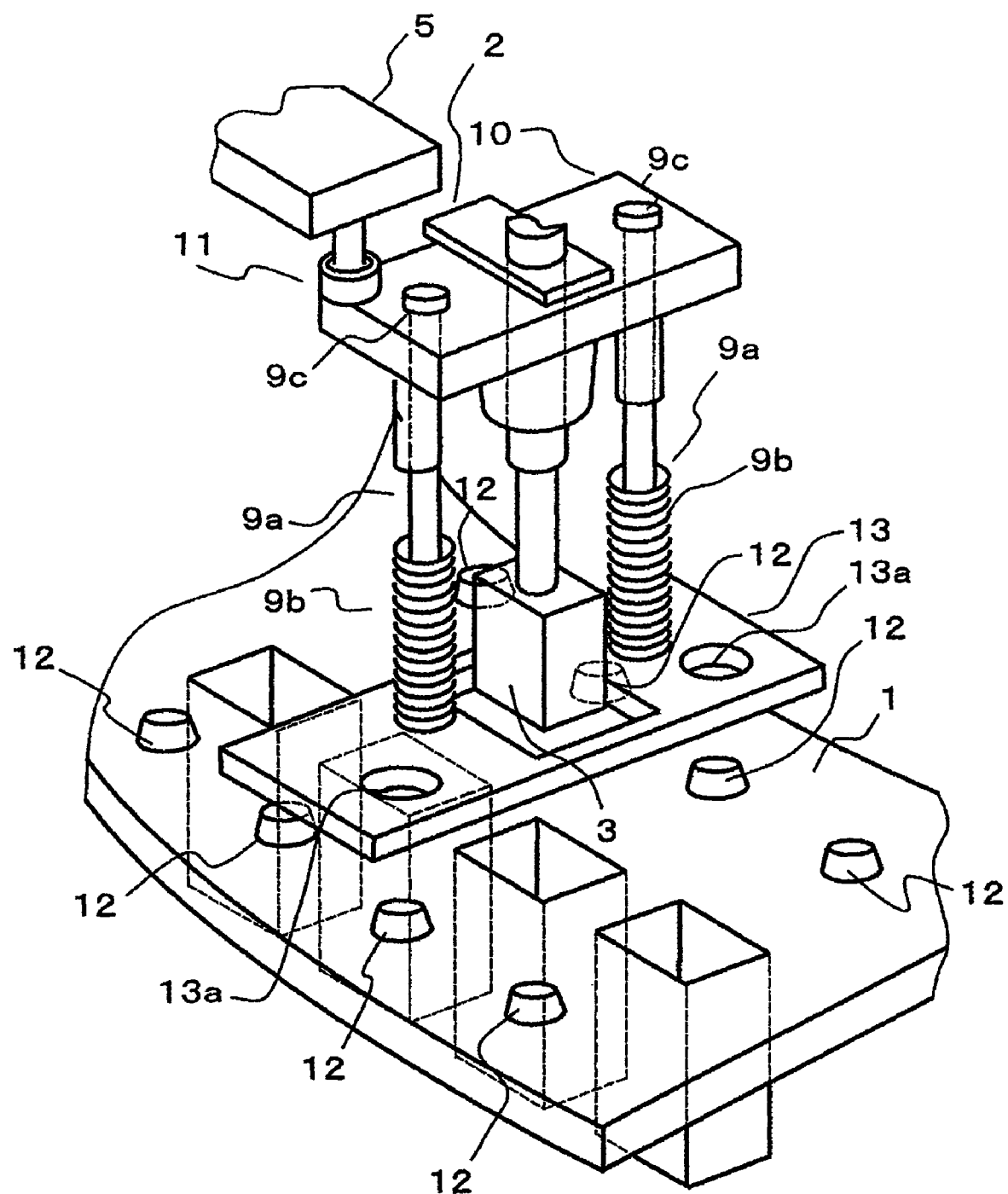
FIG. 7 is a diagram showing a state in which rinse water is not suctioned in a second embodiment of the present invention.
Figure 8:
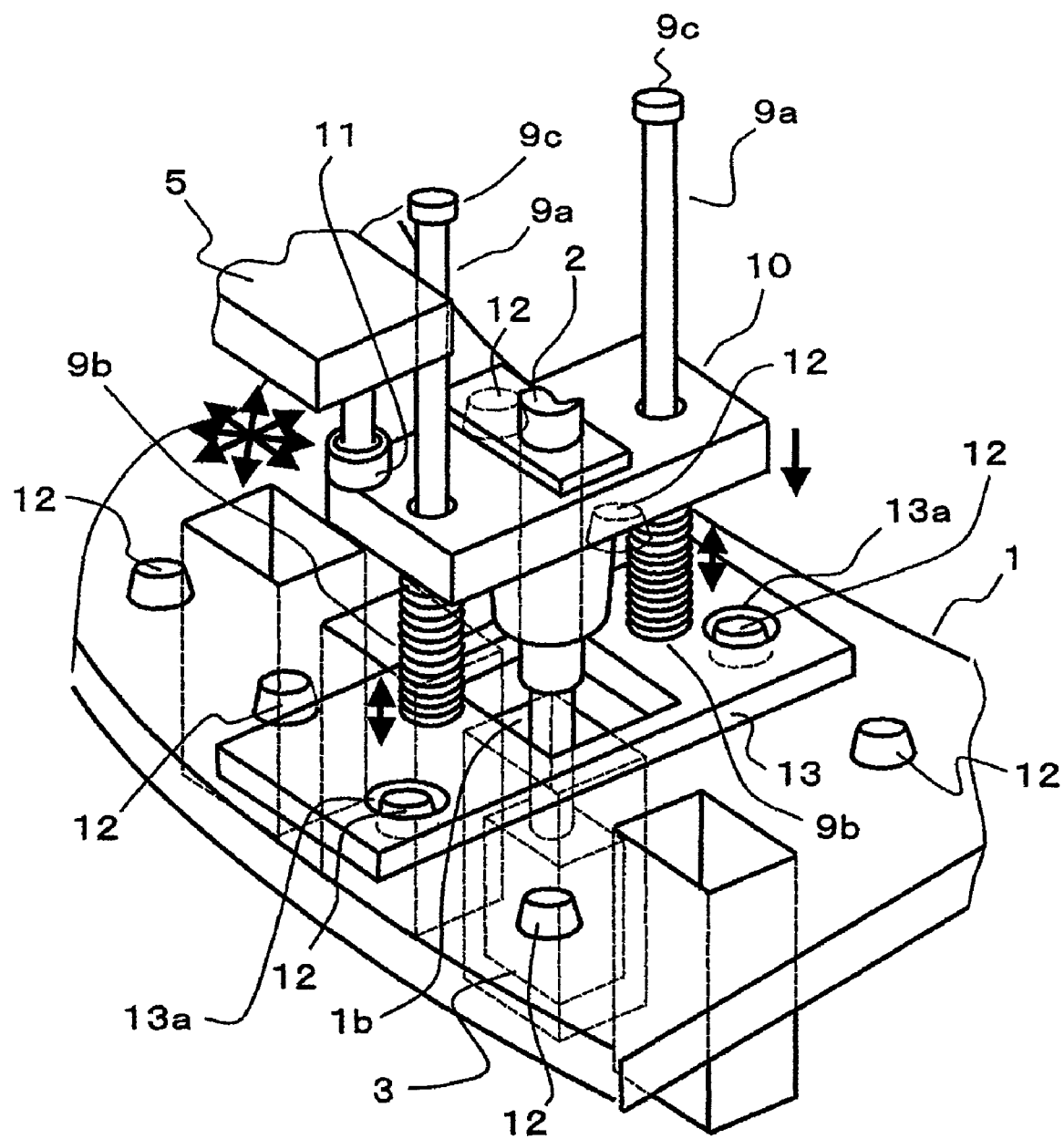
FIG. 8 is a diagram showing a state in which rinse water is suctioned in the second embodiment of the present invention.

FIGS. 7 and 8 illustrate another embodiment of the present invention. Referring to FIG. 7, the reaction cuvette 1 includes a convex (or concave) positioning guide pin (or tapered hole) 12. Also, a positioning member 13 has a concave (or convex) tapered hole (or guide pin) 13a at a position matching a positional relationship of the positioning guide pin 12. As in FIG. 5, when rinse water is not suctioned, the positioning member 13 is positioned to be lower than the suction member 3. FIG. 8 shows a state of the rinse mechanism when rinse water is suctioned. In this state, as in the state of FIG. 2, the arm 5, the nozzle support jig 10, the rinse nozzle 2, and the suction member 3 move downward. At this time, although the positioning member 13, the shaft 9a, the spring 9b, and the retainer 9c also descend, since the positioning member 13 is present at a position lower than that of the suction member 3, the positioning member 13 approaches the reaction cuvette 1 earlier. The positioning member 13 descends to the positioning guide pin 12 adjacent to the reaction cuvette position 1b into which the suction member 3 is inserted. At that time, the concave (or convex) tapered hole (or guide pin) 13a is inserted at the position matching the positional relationship of the convex (or concave) positioning guide pin 12 provided on the reaction cuvette 1. In addition, as in the above embodiment, a wide clearance is formed between the positioning guide pin 12 and the concave (or convex) tapered hole 13a in the positioning member 13. Hence, the positioning member 13 can easily enter the reaction cuvette 1 and works together with the positioning pin 12 to adjust the inserting position of the suction member 3 to the correct position. At this time, the movable part 11 assists the nozzle support jig 10 in moving horizontally. Since the suction member 3 and the reaction cuvette 1 are not changed in shape or size, the suction member 3 is thus reliably inserted into the reaction cuvette 1 without deterioration of rinse liquid suction performance and without dimensional increases of the reaction cuvette 1 or of the apparatus. Therefore, high reliability of the automatic analyzer can be achieved.

What is claimed is:

1. An automatic analyzer comprising:
   reaction cuvettes for mixing a sample and a reagent;
   a reaction disk for holding the cuvettes in order thereon, the disk being adapted to transfer a cuvette to a rinsing position;
   a rinse nozzle for suctioning rinse liquid from the cuvette transferred to the rinsing position;
   a suction member connected to the nozzle; and
   a shifter for moving the nozzle in a vertical direction; and
   a first positioning guide mounted on one side of the nozzle and a second positioning guide mounted on an opposite side of the nozzle; and
   wherein the first positioning guide is positioned over a first cuvette on the one side of the nozzle and the second positioning guide is positioned over a second cuvette on the opposite side of the nozzle whereby the position guides are inserted into openings of the first and second cuvettes when the shifter inserts the nozzle into the cuvette transferred to the rinsing position,
   the position guides being inserted into the openings of the first and second cuvettes prior to the nozzle being inserted into the cuvette transferred to the rinsing position.

2. An automatic analyzer according to claim 1, wherein the positioning guides are guide pins having tapered tips.

\* \* \* \* \*